(12) United States Patent
Haidegger et al.

(10) Patent No.: US 10,977,926 B2
(45) Date of Patent: Apr. 13, 2021

(54) METHOD FOR THE DISINFECTION AND THE QUALITY CONTROL OF THE DISINFECTION OF THE HANDS OF A USER AND APPARATUS FOR CARRYING OUT THE METHOD

(71) Applicant: HANDINSCAN ZRT., Debrecen (HU)

(72) Inventors: Tamás Péter Haidegger, Budapest (HU); Péter Szerémy, Pécs (HU); Ákos Lehotsky, Budapest (HU); Gergely Major, Tata (HU); Bence Takács, Zalaszabar (HU); Péter Róna, Biatorbágy (HU)

(*) Notice: Subject to any disclaimer, the term of this patent is extended or adjusted under 35 U.S.C. 154(b) by 19 days.

(21) Appl. No.: 16/322,905

(22) PCT Filed: Dec. 13, 2017

(86) PCT No.: PCT/HU2017/050055
§ 371 (c)(1),
(2) Date: Feb. 1, 2019

(87) PCT Pub. No.: WO2018/109507
PCT Pub. Date: Jun. 21, 2018

(65) Prior Publication Data
US 2019/0172336 A1 Jun. 6, 2019

(30) Foreign Application Priority Data
Dec. 14, 2016 (HU) .................................. P1600669

(51) Int. Cl.
*G08B 21/24* (2006.01)
*A61L 2/18* (2006.01)
(Continued)

(52) U.S. Cl.
CPC .............. *G08B 21/245* (2013.01); *A61L 2/18* (2013.01); *A61L 2/24* (2013.01); *A61L 2/26* (2013.01);
(Continued)

(58) Field of Classification Search
CPC . G08B 21/245; A61L 2/18; A61L 2/24; A61L 2/26; A61L 2202/122; A61L 2202/14; A61L 2202/15
(Continued)

(56) References Cited

U.S. PATENT DOCUMENTS 5,960,991 A * 10/1999 Ophardt .............. A47K 5/1217
222/1
8,245,877 B2 * 8/2012 Ophardt .............. A47K 5/1217
222/1
(Continued)

*Primary Examiner* — Huy Tram Nguyen
(74) *Attorney, Agent, or Firm* — Handal & Morofsky LLC; Anthony H. Handal

(57) ABSTRACT

Method for the disinfection and the quality control of the disinfection of the hands of a user comprising the steps of:
dispensing a predetermined amount of the mixture of a disinfectant substance and a light reflection modifying substance on the hands to be disinfected,
allowing the user to smear and rub the mixture on his/her hands,
inserting the hands one after the other into an imaging compartment (11) of an apparatus (10) for disinfection quality control;
illuminating the inserted hand with light sources (14) emitting light having a predetermined spectral distribution and intensity;
recording the image of the hand (9) from both sides by cameras (16);
processing the recorded image to provide distinction between areas of the hand contacted and non-contacted by the mixture, wherein the light reflection modifying
(Continued)

substance is a substance that absorbs light in at least a predetermined range a wavelength which is added to the disinfectant substance in an amount that decreases light absorption of areas treated by the mixture and retains at the same time disinfectant properties; the light source emits light to cover the predetermined range and the cameras have sensitivity in that range, furthermore, in the processing step areas of the hand (9) are made brighter which were not contacted previously by the mixture.

12 Claims, 4 Drawing Sheets

(51) Int. Cl.
*A61L 2/24* (2006.01)
*A61L 2/26* (2006.01)

(52) U.S. Cl.
CPC ..... *A61L 2202/122* (2013.01); *A61L 2202/14* (2013.01); *A61L 2202/15* (2013.01)

(58) Field of Classification Search
USPC .......................................................... 422/292
See application file for complete search history.

(56) References Cited

U.S. PATENT DOCUMENTS

| | | | |
|---|---|---|---|
| 2004/0083547 A1* | 5/2004 | Mercier | A47K 5/1217 4/623 |
| 2005/0134465 A1* | 6/2005 | Rice | A61B 90/96 340/573.1 |
| 2006/0092315 A1* | 5/2006 | Payonk | H04N 5/2354 348/370 |
| 2007/0117042 A1* | 5/2007 | Barr | G03C 1/77 430/270.1 |
| 2007/0206098 A1* | 9/2007 | Matsuo | G06K 9/2018 348/207.99 |
| 2008/0094478 A1* | 4/2008 | Sato | H04N 5/232945 348/208.12 |
| 2009/0292195 A1* | 11/2009 | Boyden | A61B 5/021 600/407 |
| 2013/0215245 A1* | 8/2013 | Haidegger | G08B 21/24 348/77 |

* cited by examiner

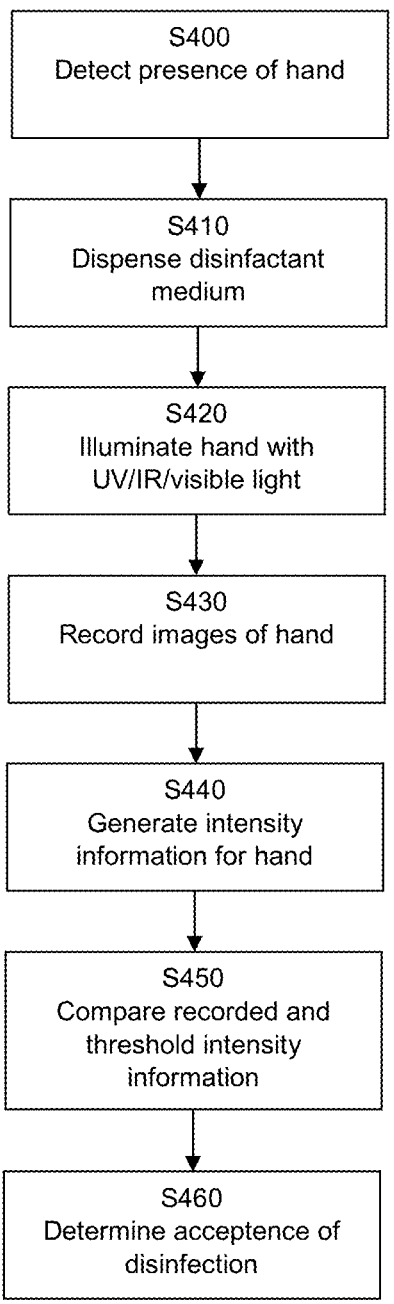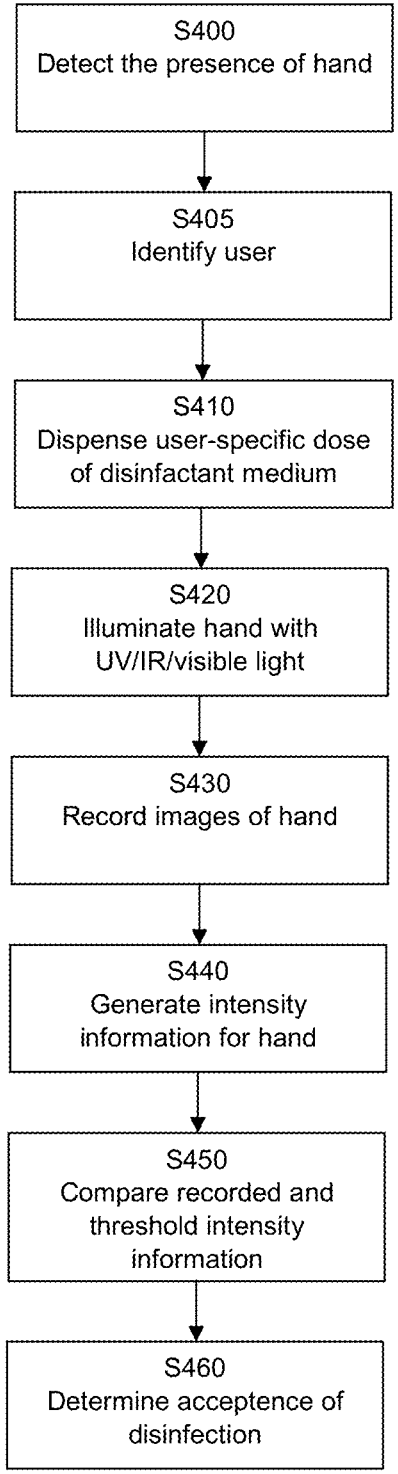
FIG. 4A
FIG. 4B

METHOD FOR THE DISINFECTION AND THE QUALITY CONTROL OF THE DISINFECTION OF THE HANDS OF A USER AND APPARATUS FOR CARRYING OUT THE METHOD

TECHNICAL FIELD

The invention relates to a method for the disinfection and the quality control of the disinfection of the hands of a user and apparatus for carrying out the method.

BACKGROUND OF THE INVENTION

Hospital-acquired infections (HAI), also referred to as healthcare-associate infections or nosocomial infections, are one of the leading causes of death in the United States and Europe. The major source of HAI is the improper hand disinfection. HAI generate unnecessary expenses, reduces the quality of life of the patients, prolongs recovery and promotes the resistance of pathogens against antibiotics. Furthermore, hand hygiene has outstanding importance at nursing homes, veterinarian clinics, clean manufacturing plants, biotechnological production, food service stations and in the hospitality industry.

The applied methods of hand disinfection have been widely discussed in recent studies such as in Behre M. et al., "Measurement and feedback of infection control process measures in the intensive care unit: impact on compliance" (American Journal on Infection Control, Vol. 34, no. 8, 2006, pp. 537-539), World Health Organization (WHO) Guidelines on Hand Hygiene in Health Care (WHO First Global Patient Safety Challenge Clean Care is Safer Care, 2011) and (Centers for Disease Control and Prevention) CDC guidelines (How-to Guide: Improving Hand Hygiene A Guide for Improving Practices among Health Care Workers, CDC, 2006). However, despite the numerous disinfection stations and the spread of antibacterial soaps, the insufficient hand washing remains a major problem in health care and causes several infection-related problems at general households as well. In the medical environment, appropriate hand disinfection is required to keep HAI rates low, especially as the new mutant germs—such as the Methicillin-resistant Staphylococcus aureus (MRSA), New Delhi metallo-beta-lactamase 1 (NDM-1), Carbapenem-resistant enterobacteriaceae (CPE)—show high resistance to antibiotic treatment. Also in the general practice, proper hand hygiene helps to maintain a healthy life, and to prevent or reduce the spread of epidemics (e.g., Severe Acute Respiratory Syndrome (SARS), Influenza A (H1N1), etc).

Document US 2013/0215245 A1 discloses a method for hand disinfection quality control, the method comprising the steps of providing a hand disinfectant medium containing light reflecting particles responsive to light mostly outside the visible spectral range of light, applying the hand disinfectant medium on the hands in a prescribed manner for a prescribed time, and illuminating the treated hands by means of a light source providing light in a spectral range for activating the reflecting particles. The method further comprises the steps of recording digital images of the hands from both sides, and evaluating the recorded images by a computer program, in order to determine the extent of cleanness of the hands. The aforementioned document also discloses an apparatus for implementing the aforementioned method and assessing hand disinfection quality. The apparatus comprises a rigid case with side walls enclosing a light source for providing light of a predetermined spectral range mostly outside the visible range. The case is further provided with an opening on the front wall for receiving the hands to be exposed to the light of the light source. An imaging device is also attached to the case for taking images of the illuminated hands.

The above described method and apparatus have the drawback that the use of light reflective particles in the disinfectant medium allows only a negative signaling method, wherein the presence of the disinfectant medium on the hands provides high intensity in the recorded images, whereas the untreated areas appear with low intensity in the images and therefore these regions are often hardly distinguishable from the background of the recorded image. This means that the untreated regions are just hard to be exactly identified.

A further drawback of the above method is that the light reflective particles, which are typically UV-reflective particles, can also be easily observed visually, thus the light reflective particles that are not removed from the hands after their treatment, can still be seen under UV light. This might be inconvenient for those who must stay at a place where UV light is necessary to be used (e.g., in clubs, tanning salons, in front of some windows, etc), moreover it prevents further objective measurements until the UV-reflective particles are completely removed from the hand.

It is an object of the present invention to provide a method and a device which enables a faster and more efficient disinfection of the hands of medical doctors, nurses and other medical staff and which is free of unwanted detectable tracks on the hands, and the device is not only good for controlling the quality of disinfection but takes a record about it.

SUMMARY OF THE INVENTION

These and other objects are achieved by providing a method for the disinfection and the quality control of the disinfection of the hands of a user and apparatus for carrying out the method comprising the steps as described in the attached method claims 1 to 5. The apparatus according to the invention is designed as claimed in claims 6 to 12.

The method and the apparatus according to the present invention allow an accurate and objective identification of the disinfected areas on a treated hand and for the perfect disinfection by allowing repeated disinfection of the previously determined untreated areas.

BRIEF DESCRIPTION OF THE DRAWINGS

The invention will now be described in connection with examples and embodiments thereof in which reference will be made to the accompanying drawings. In the drawing:

FIG. 1A shows a simplified how the disinfection substance is dispensed on the hands of a user;

FIGS. 4A and 4B are flow diagrams of the steps of the method.

The method according to the invention is based on the discovery that the quality of the disinfection can be checked in a faster, easier and more reliable way if during the control carried out according to the present invention the non-disinfected portions of the hands will distinctively appear and show the zones or areas where a second or additional disinfection is required. This can be attained if a light absorbing substance is added to the conventional disinfecting material, which decreases the light reflection of the so disinfected skin surfaces areas at a predetermined range of wavelengths, therefore if the hand or hands is/are illuminated with light source emitting light in this predetermined range, then the areas of the hand which have got into contact with the substance will appear pale or less visible compared to the areas which have not get into contact with the disinfectant. In this way the more intensive light reflection of the non-disinfected areas will appear as visible light zones on a display screen, especially if appropriate picture processing steps enhance the differences between pale and more intensive areas.

The added light absorption substances should not influence the disinfectant properties of the liquid or gel to which they are added, and the decreased light absorption should persist through a certain period of time (e.g. at least 3 minute but can persist longer i.e. through 15 to 30 minutes).

Of course, the light absorbing properties of the added substance can be wavelength-dependent therefore the illumination of the hand should be done by a light source that emits rays predominantly in the most absorbing range of wavelength of the substance used and the so illuminated hands should be observed by cameras which have high sensitivity in this range of wavelengths.

Figure 1A:
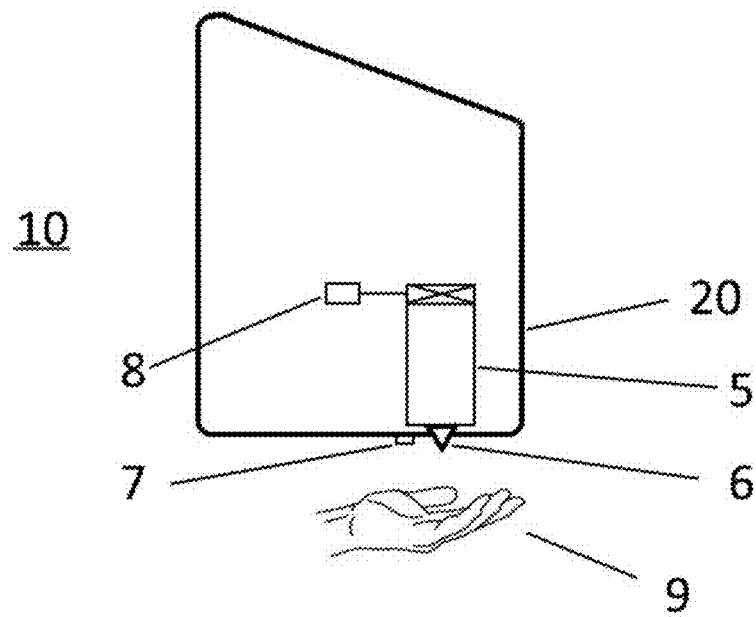
FIG. 1A shows a schematic detail how the disinfectant substance is dispensed on the hands.

Reference is made now to FIG. 1A which schematically illustrates the way how the disinfectant substance is dispensed to the hands to be disinfected. It is preferred if a hand disinfection unit is part of an apparatus 10 which enables disinfection, quality control of the disinfection process and provides an appropriate visual feedback for the person under disinfection to enable him disinfecting the previously left out areas of his/her hands.

The apparatus 10 has housing 12 of which only a separate portion is illustrated in FIG. 1A that comprises an electronically controlled dispenser 5 filled with a predetermined volume of disinfectant substance to which the absorption decreasing substance has been previously admixed, and has a dosage vent 6 at the lower end through which a preset volume of disinfectant substance is discharged (or sprayed) to the hands of the treated person. A proximity sensor 7 is arranged at the lower surface of the housing 12 which allows feeding of the substance only if hands 9 of a user are in an appropriate position under the dosage vent 6. A dispenser control unit 8 is illustrated that is connected with other blocks of the apparatus 10, and it can be assumed that the dispenser control unit 8 receives information on the volume of the disinfectant to be dispensed to the particular user who stands in front of the apparatus 10.

The disinfectant substance is a mixture of a conventional disinfectant composition including at least 60% of ethanol or isopropyl alcohol and may contain additional components like e.g., glycerin, gelling agent and scent substances, etc. and water.

For the method according to the invention a light absorbing chemical substance is added to such disinfectant before use. A few examples for such a light absorbing substance which have maximum light absorbing effect in different wavelength ranges of light are as follows:

A substance that has maximum light absorbing property in the ultraviolet (UV) range of wavelength can be Avobenzone that has a CAS registration number: 155633-54-8, which should be added to the disinfectant substance in about a concentration of 10%.

A substance that has maximum light absorbing property in the infrared (IR) range of wavelength can be Indocyanine green that has a CAS registration number: 3599-32-4, which should be added to the disinfectant substance in a concentration of about 1%.

A substance that has maximum light absorbing property in the visible range of wavelengths can be Fluorescein that has a CAS registration number: 2321-07-05, which should be added to the disinfectant substance in a concentration of about 2%.

The indicated concentration values of the light absorbing material depend on several parameters, including temperature, viscosity and the composition of the disinfectant substance to which it is admixed; therefore these values were given for orientation purposes only. A "sufficient degree" of the decrease of light absorption means that there is a definitely different light reflection from the skin areas that were previously contacted by a disinfectant containing the absorption decreasing substance compared to surface areas which have not been contacted by that material. In practice, a drop in light reflection equal to or more than 50% is considered as sufficiently distinctive.

Following the dispensing of the metered amount of such a disinfectant substance on the hands of the subject, the hands are moved to distribute the substance along the skin surface as in case of normal hand rubbing or hand-washing with a detergent or soap. Following a thorough hand washing type movement the disinfectant evaporates fast and in principle the hands are considered to be disinfected. This operation lasts for a few tens of seconds or minutes and before the subject would be allowed to proceed to the clean area to perform e.g. a surgery, the quality of the disinfection should be checked.

Figure 1B:
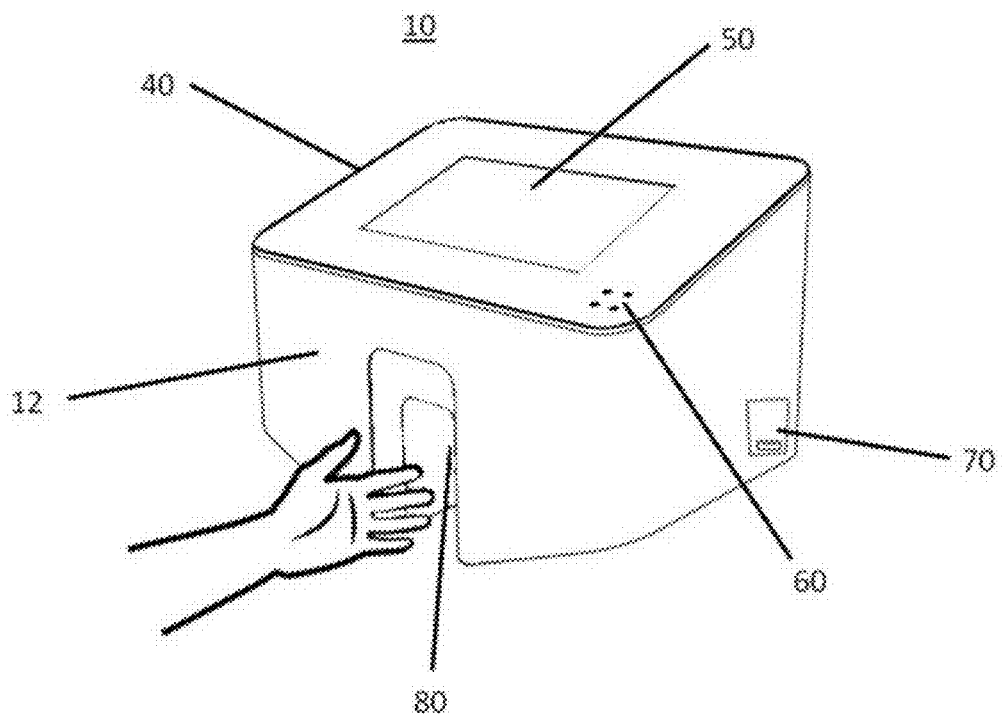
FIG. 1B shows the simplified perspective view of the apparatus.
Figure 2A:
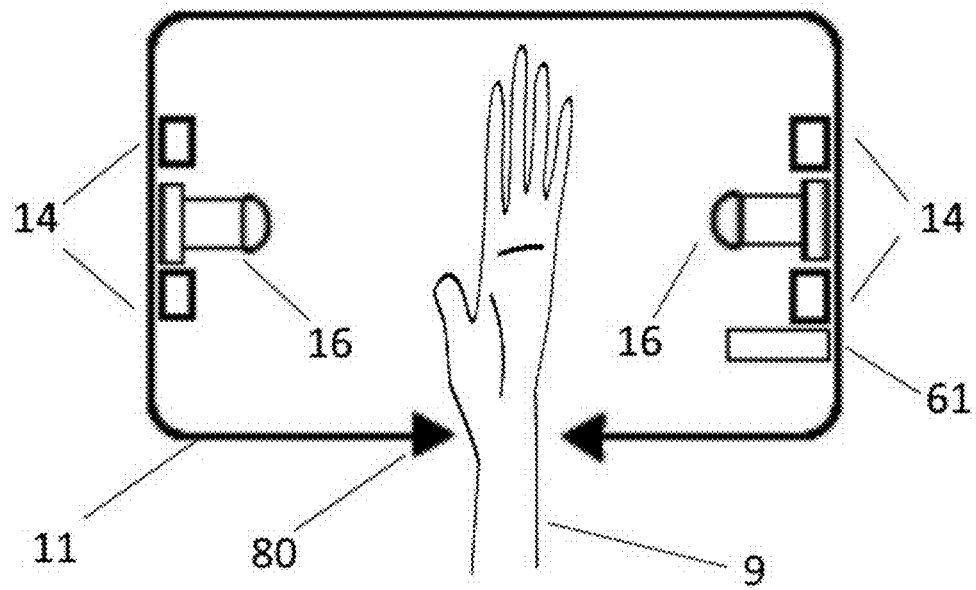
FIG. 2A shows the top view of the imaging compartment 11.
Figure 2B:
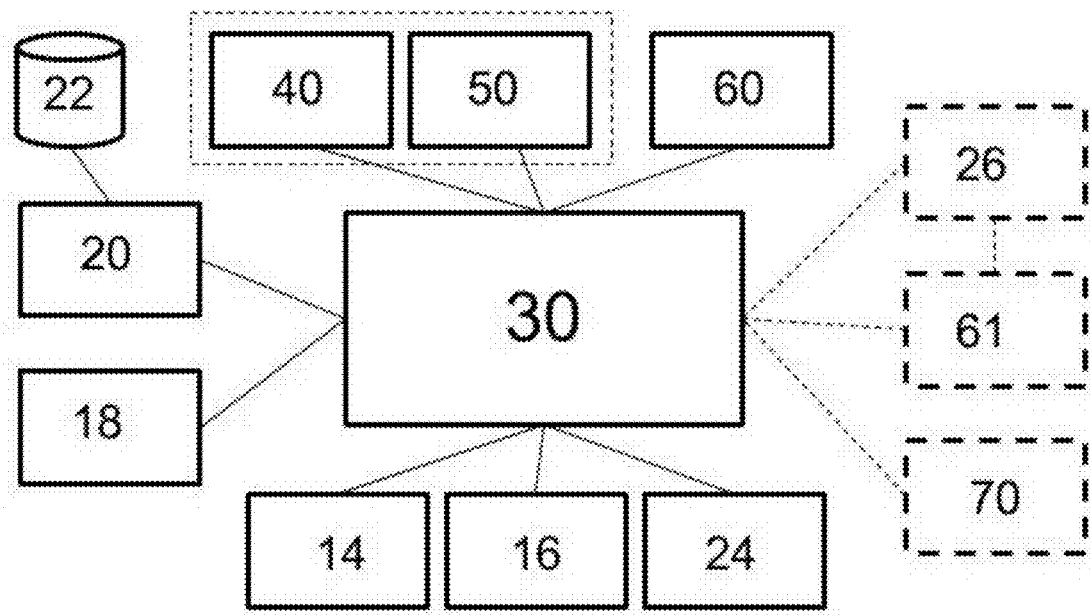
FIG. 2B shows the block diagram of the apparatus.

Absorption-based imaging allows for the detailed analysis of the region-of-interest on the hands 9. Owing to the presence of the absorption decreasing substance in the disinfectant when a hand 9 is illuminated with light that has the required spectral distribution the visibility of the areas where the disinfectant contacted the skin will have a decreased intensity level compared to those skin zones which escaped contact with the disinfectant. FIGS. 1B and 2A and 2B show further parts of the apparatus 10 in which FIG. 1A shows the simplified perspective view of the apparatus 10, FIG. 2A illustrates schematically the top view of a part of the housing 12 in which a hand 9 is inserted for checking the quality of the previous treatment by the disinfectant material, and FIG. 2B is the block diagram of different parts of the apparatus 10.

The housing 12 is preferably designed as a rigid, wall-mountable box that can be made of a light metal such as aluminum or any plastic material with similar properties to ensure rigidity while facilitating mobility of the apparatus 10 due to its light overall weight and it is easy to be cleaned. On its outer surface or as separate units the apparatus 10 further comprises a connection to an input means 40 for locally controlling the operation of the apparatus 10 by a user or an inspecting personnel, a built in or separately connected display means 50 for displaying visual information for the user, one or more status indicators 60 for producing visual or audible status signals representing operating modes of the apparatus 10 and/or disinfection quality control test results. At a front side of the apparatus 10 an inspection cavity 80

(or slot) is provided into which the hands 9 of a user should be inserted one after the other for quality control.

The top view of FIG. 2A shows an imaging compartment 11 formed as a box when a hand 9 of the user is inserted through the inspection cavity 80. Inner walls of the imaging compartment 11 are painted black or covered by non reflecting paint or material so that light will not be reflected from it. In addition to these properties the surfaces of the walls of the imaging compartment 11 may be treated with an antibacterial coating or may be made of an anti-bacterial material for minimizing infection transfer from one user to another user in case of intensive use of the apparatus 10 by a plurality of users.

In the imaging compartment 11 around two sides of the hand 9 a number of light sources 14 are provided which are arranged and oriented so that all parts of the hand 9 will be evenly illuminated by them. Similarly, several cameras 16 are arranged within the imaging compartment 11 which are directed to all parts of the hand 9 and have the task of taking pictures on the whole skin surface area. The spectral distribution of the light 14 and the spectral sensitivity of the cameras 16 should be coordinated so that they correspond to the maximum absorption range of wavelength of the chemical substance added to the disinfectant used by the apparatus 10. This can be achieved by using light source 14 that emit light in the required spectral range or by using special filters on the light sources which are transparent mainly for the required range. The same concerns the spectral sensitivity of the cameras 16 which can be realized by using appropriate filters.

It is important to adjust the intensity of the light sources 14 and the sensitivity of the cameras 16 in such a way that a well recognizable (sharp) picture is obtained in case of viewing bare skin which has not been treated previously with light absorbing material, and to have much darker picture from skin areas treated previously by the disinfectant comprising the light absorbing substance. This can be set electronically by appropriate adjusting sensitivity thresholds of the imaging system.

This adjustment differs substantially from the adjustment conditions as used in the cited prior art where light reflected from non-treated zones of the skin had to be made non-visible or hardly visible in order to make the areas covered with light-reflecting materials well visible.

In the interior of the imaging compartment 11 a hand proximity sensor 18 may also be arranged which has the task of indicating when a hand 9 is present and measurement can take place.

FIG. 2B shows the general block diagram of the apparatus 10. We can see in blocks the elements already described i.e. the light sources 14, the digital cameras 16, the hand proximity sensor 18, a separate dispensing unit 20 (shown also in FIG. 1A) that also comprises a container 22 for storing the disinfectant medium, a data storage unit 24 and a processor unit 30 configured to operate the whole apparatus. Preferably, the apparatus 10 further comprises the interface unit 70 for connecting the apparatus 10 with another external device, like a personal computer or a laptop, directly or through a communication network, for locally or remotely supervising the operation of the apparatus 10 and for allowing external evaluation of the utilization of the apparatus by the users. In case the apparatus comprises a wired interface unit 70, an interface connector, e.g., a USB port, is provided on a wall of the apparatus. Preferably, the apparatus may contain a user proximity sensor 61 to trigger a measurement or initiate an action on its screen.

In a particularly preferred embodiment of the apparatus 10, an RFID-based or other touchless personal identification module 26 may be provided. In this embodiment, the personal identification module 26 is activated by the user proximity sensor 61 when an authorized user approaches the apparatus to a certain distance.

In order to assure an acceptable speed of image processing (preferably within a few seconds), the captured images may be downsized (without significantly affecting the segmentation accuracy), then filtering may be carried out. Out of the three intensity channels (corresponding to red, green and blue (RGB or HSV channels), one may be used for finding the region of interest (segmenting the entire hand) and another one may be used for image processing, to classify the pixels (segmenting the clean areas). In order to separate the pixels belonging to treated and untreated regions of the hand, a quick segmentation algorithm is to be applied that may be fed with the histogram of a single-channel input image. Finally, pixel-based filtering, region-based filtering and weighting are used to produce the final image information which can be processed for display and sanitation quality control. This final image information may include, for example, a visual overlay of the treated areas and the entire hand in 2D or in 3D with associated numeric details, the percentage of the treated areas relative to the entire hand surface, and an objective quality score for the efficiency of the whole hand disinfection. These and other useful pieces of information of the disinfection quality control processing may be displayed on the display 50. Optionally, sound effects may also be generated to present audible indications of pass/fail events.

Due to the above mentioned features of the inspection cavity 80 of the apparatus 10 according to the invention, the UV or IR light absorbing areas of the treated hand will be clearly distinguishable from the untreated, UV or IR reflecting areas of the hand in the images recorded by the cameras 16.

The hand proximity sensor 18 is adapted to detect the presence of a hand within the inspection cavity 80. The hand proximity sensor 18 may be any type of proximity sensor, including optical sensors, ultrasound sensors, radio frequency sensors an so on. The hand proximity sensor 18 is preferably integrated into a wall of the imaging compartment 11.

The apparatus 10 may also be equipped with a user proximity sensor 7 or 61 to detect if someone approaches the apparatus 10 or stands in front of it. The user proximity sensor 61 is used to trigger the operation of the apparatus, for example, to start a training presentation of how to use the apparatus 12 or how to correctly sanitize the user's hand. It is noted that these functions may be provided in other ways as well, for example by means of an activation button (not shown) mounted on the external wall of the case of the apparatus.

The dispenser 20 is used to dispense the disinfectant medium stored in the container 22 in predetermined doses by means of a calibrated pump. The disinfectant medium may be in the form of a liquid, a gel or soap. The dispensed amount of the disinfectant medium may be determined on the basis of the identity of the user, the hand size, the location of use of the device or any other preference of the operator. Dispensing mechanisms suitable for electronically controlled, metered dosage of an agent are well known in the art. The disinfectant medium as explained earlier is a special mixture of a light absorbing material and a conventional alcohol-based disinfectant. Processor unit 30 is configured to operate the whole apparatus 10 by receiving signals from the hand proximity sensor 18 and the input means 40, and by controlling the operation of the light sources 14, the at least one camera 16, the display 50, the status indicators 60 and the dispenser 20. The processor unit 30 is also adapted for controlling the recording, recalling and transmitting of data from/to the internal data storage unit 24, or from/to any external data storage unit.

The input means 40 include any means suitable to input control information or other user data into the apparatus 10. In a particularly preferred embodiment of the apparatus 10 according to the invention, the input means 40 and the display 50 may be provided in an integrated form, for example as a touch-screen, or may be formed as a part of a hand-held electronic device, such as a smart phone or a PC.

The images recorded by the camera(s) 16 may be transmitted to an external processor device, such as a personal computer or a portable notebook attached to the optional wired (e.g. USB) or wireless (e.g. WiFi, Bluetooth, ZigBee etc.) interface unit 70 of the apparatus, and the external processor device may perform an automatic evaluation procedure, providing images of enhanced quality that highlights the difference between the treated areas and the untreated areas of the hand, and further provides overall quantitative and/or qualitative information with respect to the ongoing hand sanitization process. Locally computed results and data may also be transmitted to an external processor and/or storage unit.

Beyond the visual presentation of the results of the hand sanitation process, the data resulted from the image processing may be forwarded to (through the optional interface unit 70) and stored in a central database, therefore an external processing device may further process and evaluate the hand sanitation information provided by the apparatus. For example, statistics over the hand hygiene performance of a plurality of users may be established and made available for an infection control staff or the management of a health care institute.

Furthermore, it may be useful to build an initial database of typical user hands to calibrate the algorithm for the individual hand and skin properties (such as tone, birth marks, vessels, etc.). This ensures the robustness of the evaluation procedure, and may also determine the required dosage of disinfectant medium to be dispensed at every use. Basically, each user's hands should be recorded in a completely untreated state. On this kind of initial image, special skin features can be identified, and their locations may be stored relatively to the segmented hand of the user.

The wireless communication may allow the apparatus 10 to automatically switch to preset parameters during the image processing, when a registered user is identified at using the apparatus. Otherwise, the image recording and processing software of the apparatus runs using a generic set of parameters (i.e. default mode), without specifically edged for the actual user.

According to a preferred embodiment, the apparatus may further comprise a user identification module for recording identity of the user whose hand is subject to disinfection quality control, wherein the user identification module may be based on the use of any one of the personal identification technologies including magnetic card, smart card, RFID, ultrasound or infrared (IR) identification.

The display 50 may be configured to present user-specific information, special educational materials, video training, preferably according to the given user identified by the user identification module.

Furthermore, the apparatus 10 may be equipped with loud speakers for presenting audio instructions to the user during the hand disinfection process.

FIG. 4A shows a flow diagram of the steps of the operation of the apparatus in accordance with the present invention. For the method, it is assumed that the user proximity sensor 61 has already detected the presence of the user in front of the apparatus, or the user made a clear indication of its intention to use the apparatus 10 (e.g., by applying his or her RFID to the RFID reader or entering a personal identification (PIN) code on the touch screen).

In a first step S400, the presence of an identified user's hands 9 is detected under the dosage vent 6 of the dispenser 5 by means of the hand proximity sensor 7 of the apparatus.

In a further step S410 of the method, a hand disinfectant medium comprising the light absorbing material is dispensed onto the hands 9 of the identified user in a specific dose. The amount of the dose of the medium can be read from the internal or external data storage unit, and forwarded to the pump of the dispenser, which dispenses the specified amount of disinfectant medium on the hands of the user.

After the user has distributed the disinfectant medium on the entire surface of his or her hands 9, a first hand should be inserted for quality control purposes into the inspection cavity 80 of the apparatus 10, the inserted hand 9 is illuminated by the light sources 14 in step S420 and one or more digital images of the hand are recorded by the cameras 16 in step S430, at least from two sides of the hand 9 (e.g. palmar and dorsal). It is preferred that by using more than two cameras 16, for example four or six cameras, the entire surface of the hand 9 can be appropriately scanned in order to allow a more reliable sanitation quality control. Alternatively, 3D stereo cameras or depth sensors may also be used to obtain a 3D image of the hand 9 under inspection.

Based on the recorded images of the hands 9, intensity information is generated for the illuminated hands in Step S440 by means of the processing unit 30 of the apparatus 10, wherein said intensity provides information on the brightness of the hand surface area covered by the disinfectant medium. In a preferred embodiment of the method of the invention, the intensity information is a 2D or 3D intensity map of the illuminated hand showing the concentration distribution of the UV, visible light or IR absorbing particles over the scanned areas of the inspected hand 9. In this case the non-covered areas of the hand 9 will appear as the highest intensity areas, whereas the areas covered by the disinfectant medium show lower intensity.

Following the inspection of a first hand the same is repeated with the other hand of the user. It is important to note, that the user can see the display 50 after the pictures of the cameras 16 has been processed, and he can immediately see whether there are zones on his/her hand 9 which were not disinfected, as these areas will be easily recognizable since they are shown with higher brightness. If the user has experienced that such untreated zones exist, he/she returns to the beginning of the process and initiates a second disinfection by allowing a second dose of disinfectant to his/her hands and now, in the knowledge of the preciously uncovered areas, it is easy to make sure that these areas will receive a proper amount of disinfectant. After this second disinfection step the quality control can be repeated, and it will have a high likelihood that by now the full area of the hands will pass the quality control.

Optionally, as illustrated in FIG. 4B in step S405, the user may be identified by means of an RFID card belonging to the user or by any other personal identification technology (e.g. iris scanning, inputting PIN code, etc.). In this embodiment, i.e. when the identification of the user has been carried out, a user-specific dose of the disinfectant medium may be dispensed in step S410.

Figure 3A:
FIGS. 3A and 3B show images of a partially treated hand recorded in the spectrum of the visible light and in the UV spectrum, respectively.
Figure 3B:
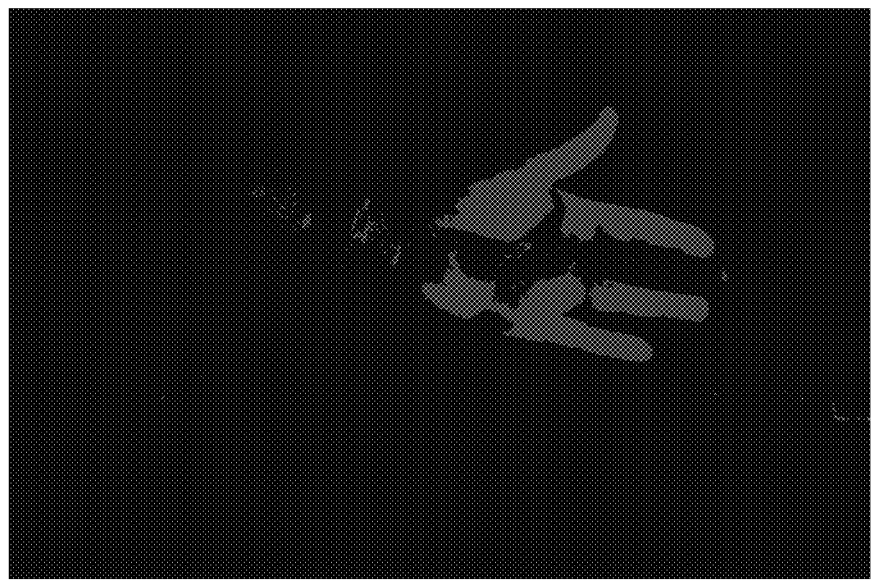

As an example, FIGS. 3A and 3B show images of a partially treated hand recorded in the spectrum of the visible light and in the UV spectrum, respectively. The hand was treated in this example only at the areas represented by the cross. As shown in FIG. 3A, the treated (UV absorbing) areas of the hand can be hardly recognised in the visible light spectrum. However, as shown in FIG. 3B, the treated areas of the hand (covered by the disinfectant medium containing an UV absorbing material) and the background of the image (corresponding to the walls of the inspection cavity) have substantially no reflective intensity (appearing in dark), whereas the untreated areas of the hand have high reflective intensity (appearing as light zones), thereby definitely showing those parts of the hand where an insufficient amount of disinfectant medium has been applied.

Then in step S450 (shown both on FIGS. 4A and 4B), the generated intensity information is compared by the processing unit 30 with predetermined or user-specific threshold intensity information, which corresponds to an acceptable hand sanitation level of the current user. This step may include the comparison of a 2D or 3D intensity map of the illuminated hand with a corresponding threshold intensity map or the comparison of an overall intensity value of the illuminated hand with a corresponding threshold overall intensity value.

Finally, it is determined in step S460 whether the quality of disinfection is acceptable or not based on the comparison of the recorded intensity map and the threshold intensity map, or by other individualized software algorithms. The recorded image data may be further processed by the apparatus and the user is informed on the result of the disinfection quality control process, for example, by displaying the result of the hand disinfection quality control test for the user on the display of the apparatus (as described earlier), or generating a respective sound effect for the user about the success or failure of the sanitization process. The recorded image data and/or the test results may be forwarded to an external processing device (e.g., a locally connected computer or a remote computer through a wired or wireless communication network) using the interface unit 70 of the apparatus 10.

The individual sanitation test results of the users may be used to build a database either locally in the apparatus 10 or remotely, in an external database. The data stored in the data base may be used for a subsequent analysis of the users' sanitation activities and evaluate the sanitation test results on a statistical basis for making further decisions with respect to the overall hand disinfection quality control scheme of a hospital, a health center or any other institute.

It is a main advantage of the method according to the invention that the quality of the disinfection increases and it is easy to correct any error occurred during a first disinfection step because the user can see the areas where a further disinfection is required. In principle only those users are allowed to proceed to the surgery area or other clean area which have passed the quality control test.

A further advantage lies in that the light absorbing substance added to the disinfectant can be removed by a simple hand washing, therefore if during the day a doctor or nurse leaves the clean area several times and returns for further work, the disinfection process can be carried out again. In prior art methods the light reflecting components remained on the hand for a longer period and could not be removed by a simple hand washing, which rendered the repeated use of the method difficult or impossible.

The invention claimed is:

1. Method for the disinfection and the quality control of the disinfection of the hands of a user comprising the steps of:
dispensing a predetermined amount of a mixture of a disinfectant substance and a light reflection modifying substance on the hands to be disinfected,
allowing the user to smear and rub the mixture on his/her hands,
inserting the hands one after the other into an imaging compartment of an apparatus for disinfection quality control;
illuminating the inserted hand with light sources emitting light having a predetermined spectral distribution and intensity;
recording the image of the hand from both sides by cameras;
processing the recorded image to provide distinction between areas of the hand contacted and non-contacted by the mixture,
wherein said light reflection modifying substance is a substance that absorbs light in at least a predetermined range of wavelength, said substance is added to the disinfectant substance in an amount that increases light absorption of areas treated by the mixture and retains at the same time disinfectant properties; said light source emits light in said predetermined range of wavelength and said cameras have sensitivity in said range, wherein following in said processing step areas of said hand which were not contacted previously by the mixture, appear brighter in the recorded image.

2. The method as claimed in claim 1, wherein following said processing step showing the processed picture of the hand to the user to enable him/her to perform a second disinfection where the displayed, previously not treated lighter areas will be contacted by the mixture.

3. The method as claimed in claim 1, wherein Avobenzone that has a CAS registration number: 70356-09-1 is used as a light absorbing substance having absorption properties in the ultraviolet (UV) range of wavelength and this substance is added to the disinfectant substance in about a concentration of 10%.

4. The method as claimed in claim 1, wherein Indocyanine green that has a CAS registration number: 3599-32-4 is used as a light absorbing substance having absorption properties in the infrared (IR) range of wavelength and this substance is added to the disinfectant substance in a concentration of about 1%.

5. The method as claimed in claim 1, wherein Fluorescein that has a CAS registration number: 2321-07-05 is used as a light absorbing substance having absorption properties in the visible range of wavelengths and which should be added to the disinfectant substance in a concentration of about 2%.

6. An apparatus for hand disinfection quality control for carrying out the method as claimed in claim 1 comprising:
a housing,
a hand inspection cavity formed on a front face of the housing and adapted for receiving a hand of a user and leading to an imaging compartment,
a plurality of light sources emitting light in the absorption spectral range of wavelengths of said light absorption increasing substance, said light sources are arranged in the imaging compartment to direct light to the whole surface of the hand in said imaging compartment, digital cameras arranged in said imaging compartment being sensitive in said range of wavelength to take images of said illuminated hand, an image processing and evaluating processor unit to provide an image or visual representation of said hand showing areas not contacted by said mixture as bright areas compared to areas contacted by said mixture; and a display means to show said processed image, wherein the visual representation of the hand provided by said processed image shows areas of the hand as brighter areas not contacted by said mixture of disinfectant compared to areas contacted by said mixture of disinfectant.

7. The apparatus as claimed in claim 6 further comprising:

input means for locally controlling the operation of the apparatus, an internal data storage unit, a hand proximity sensor configured to detect presence of a hand of a user within said hand inspection cavity, wherein the processor unit is configured also to process said visual representation by using a predetermined or user-specific evaluation algorithm for determining the acceptable level of hand sanitation, and based on said evaluation to determine whether or not the quality of disinfection of the inspected hand is acceptable.

8. The apparatus as claimed in claim 6, wherein inner walls of the imaging compartment are covered with an anti reflection material having anti reflection properties in said range of wavelengths.

9. The apparatus as claimed in claim 6, further comprising one or more status indicators to produce visual or audible status signals representing operating modes of the apparatus and/or disinfection quality control test results.

10. The apparatus according to claim 6, further comprising an interface unit for connecting the apparatus to an external processor device through a wired or wireless connection.

11. The apparatus according to claim 6, further comprising a user identification module with a user proximity sensor to identify the presence of the user whose hands are subject to disinfection quality control.

12. The apparatus as claimed in claim 11, wherein the user identification module is based on the personal identification technology selected from the group of: magnetic card, smart card, RFID, NFC, fingerprint, ultrasound or infrared identification.

\* \* \* \* \*